(12) United States Patent
Matheny

(10) Patent No.: US 12,168,084 B2
(45) Date of Patent: *Dec. 17, 2024

(54) EXTRACELLULAR MATRIX (ECM) STRUCTURES FOR TISSUE REGENERATION

(71) Applicant: Elutia Med LLC, Silver Spring, MD (US)

(72) Inventor: Robert G. Matheny, Norcross, GA (US)

(73) Assignee: Elutia Med LLC, Silver Spring, MD (US)

(*) Notice: Subject to any disclaimer, the term of this patent is extended or adjusted under 35 U.S.C. 154(b) by 218 days.

This patent is subject to a terminal disclaimer.

(21) Appl. No.: 17/576,633

(22) Filed: Jan. 14, 2022

(65) Prior Publication Data

US 2022/0211907 A1  Jul. 7, 2022

Related U.S. Application Data

(63) Continuation of application No. 16/418,063, filed on May 21, 2019, now abandoned, which is a
(Continued)

(51) Int. Cl.
| | | |
|---|---|---|
| A61L 27/54 | (2006.01) |
| A61F 2/00 | (2006.01) |
| A61F 2/02 | (2006.01) |
| A61L 27/22 | (2006.01) |
| A61L 27/34 | (2006.01) |
| A61L 27/36 | (2006.01) |
| A61L 27/38 | (2006.01) |
| A61L 27/50 | (2006.01) |
| A61L 31/00 | (2006.01) |
| A61L 31/04 | (2006.01) |
| A61L 31/14 | (2006.01) |
| A61L 31/16 | (2006.01) |

(Continued)

(52) U.S. Cl.
CPC ........ *A61L 27/3629* (2013.01); *A61F 2/0077* (2013.01); *A61F 2/02* (2013.01); *A61L 27/227* (2013.01); *A61L 27/34* (2013.01); *A61L 27/3604* (2013.01); *A61L 27/362* (2013.01); *A61L 27/3625* (2013.01); *A61L 27/3633* (2013.01); *A61L 27/38* (2013.01); *A61L 27/3804* (2013.01); *A61L 27/3834* (2013.01); *A61L 27/50* (2013.01); *A61L 27/54* (2013.01); *A61L 31/005* (2013.01); *A61L 31/041* (2013.01); *A61L 31/14* (2013.01); *A61L 31/16* (2013.01); *A61N 1/375* (2013.01); *A61N 1/3752* (2013.01); *A61F 2002/0086* (2013.01); *A61F 2210/0076* (2013.01); *A61K 35/12* (2013.01); *A61K 35/22* (2013.01); *A61K 35/37* (2013.01); *A61K 35/38* (2013.01); *A61K 35/42* (2013.01); *A61K 38/005* (2013.01); *A61K 38/1825* (2013.01); *A61L 27/3679* (2013.01); *A61L 27/3683* (2013.01); *A61L 2300/20* (2013.01); *A61L 2300/23* (2013.01); *A61L 2300/25* (2013.01); *A61L 2300/252* (2013.01); *A61L 2300/40* (2013.01); *A61L 2300/404* (2013.01); *A61L 2300/406* (2013.01); *A61L 2300/41* (2013.01); *A61L 2300/412* (2013.01); *A61L 2300/414* (2013.01); *A61L 2300/418* (2013.01); *A61L 2300/434* (2013.01); *A61L 2300/45* (2013.01); *A61L 2300/64* (2013.01); *A61L 2400/02* (2013.01); *A61L 2400/12* (2013.01); *A61L 2400/18* (2013.01); *A61L 2430/20* (2013.01)

(58) Field of Classification Search
CPC ... A61F 2/02; A61F 2210/0076; A61K 35/38; A61K 35/37; A61K 35/22; A61L 27/3633; A61L 27/3683; A61L 27/54; A61L 27/3629; A61L 2300/406; A61L 2220/0075

See application file for complete search history.

(56) References Cited

U.S. PATENT DOCUMENTS

| | | |
|---|---|---|
| 4,902,508 A | 2/1990 | Badylak et al. |
| 5,275,826 A | 1/1994 | Badylak et al. |
| (Continued) | | |

FOREIGN PATENT DOCUMENTS

| | | |
|---|---|---|
| CN | 102256609 A | 11/2011 |
| WO | 2000059379 A1 | 10/2000 |
| (Continued) | | |

OTHER PUBLICATIONS

Badylak et al. "Extracellular Matrix for Myocardial Repair" Nov. 15, 2002, The Heart Surgery Forum 6(2):E20-E26.
(Continued)

*Primary Examiner* — Shin Lin Chen
(74) *Attorney, Agent, or Firm* — DLA PIPER LLP (US)

(57) ABSTRACT

The invention is to articles of extracellular matrix. The articles comprise one or more sheets of mammalian extracellular matrix laminated together. A single sheet can be folded over and laminated on 3 sides. Two or more sheets can be laminated to each other at their edges. The sheets can further encase a composition comprising a cell or cells, such as for example, a stem cell. A single sheet can be folded over to encase a composition, or rolled to encase a composition with lamination at either end of the roll, for example. The invention also includes methods of using these articles to regenerate tissue at tissue defects, or heal wounds in damaged tissue.

16 Claims, 3 Drawing Sheets

Related U.S. Application Data continuation of application No. 14/685,714, filed on Apr. 14, 2015, now Pat. No. 10,293,084, which is a continuation of application No. 14/306,368, filed on Jun. 17, 2014, now Pat. No. 9,333,277, which is a continuation of application No. 13/033,102, filed on Feb. 23, 2011, now Pat. No. 8,758,448, which is a continuation of application No. 12/394,914, filed on Feb. 27, 2009, now abandoned, which is a continuation of application No. 11/747,004, filed on May 10, 2007, now abandoned.

(51) Int. Cl.
| | | |
|---|---|---|
| *A61N 1/375* | (2006.01) | |
| *A61K 35/12* | (2015.01) | |
| *A61K 35/22* | (2015.01) | |
| *A61K 35/37* | (2015.01) | |
| *A61K 35/38* | (2015.01) | |
| *A61K 35/42* | (2015.01) | |
| *A61K 38/00* | (2006.01) | |
| *A61K 38/18* | (2006.01) | |

(56) References Cited

U.S. PATENT DOCUMENTS

| | | |
|---|---|---|
| 5,281,422 A | 1/1994 | Badylak et al. |
| 5,352,463 A | 10/1994 | Badylak et al. |
| 5,480,424 A | 1/1996 | Cox |
| 5,554,389 A | 9/1996 | Badylak et al. |
| 5,733,337 A | 3/1998 | Carr, Jr. et al. |
| 6,206,931 B1 | 3/2001 | Cook et al. |
| 6,358,284 B1 | 3/2002 | Fearnot et al. |
| 6,379,710 B1 | 4/2002 | Badylak |
| 6,689,153 B1 | 2/2004 | Skiba |
| 6,719,788 B2 | 4/2004 | Cox |
| 7,033,611 B2 | 4/2006 | Lyngstadaas et al. |
| 7,244,444 B2 | 7/2007 | Bates |
| 7,550,004 B2 | 6/2009 | Bahler et al. |
| 8,753,885 B1 | 6/2014 | Matheny |
| 8,753,886 B1 | 6/2014 | Matheny |
| 8,758,448 B2 | 6/2014 | Matheny |
| 8,785,197 B1 | 7/2014 | Matheny |
| 8,785,198 B1 | 7/2014 | Matheny |
| 8,871,511 B1 | 10/2014 | Matheny et al. |
| 8,962,324 B2 | 2/2015 | Matheny |
| 8,980,296 B2 | 3/2015 | Matheny et al. |
| 9,044,319 B2 | 6/2015 | Matheny |
| 9,066,993 B2 | 6/2015 | Matheny |
| 9,072,816 B2 | 7/2015 | Matheny |
| 9,161,952 B2 | 10/2015 | Matheny et al. |
| 9,283,302 B2 | 3/2016 | Matheny |
| 9,333,277 B2 | 5/2016 | Matheny |
| 9,532,943 B2 | 1/2017 | Matheny |
| 9,694,105 B2 | 7/2017 | Matheny et al. |
| 9,744,264 B2 | 8/2017 | Matheny |
| 10,143,778 B2 | 12/2018 | Matheny |
| 10,159,764 B2* | 12/2018 | Matheny ............... A61L 27/54 |
| 10,293,084 B2* | 5/2019 | Matheny ............... A61F 2/02 |
| 10,383,977 B2 | 8/2019 | Matheny |
| 10,512,710 B2 | 12/2019 | Matheny |
| 10,744,163 B2 | 8/2020 | Matheny |
| 10,864,233 B2 | 12/2020 | Matheny |
| 11,045,580 B2 | 6/2021 | Matheny |
| 2003/0014126 A1 | 1/2003 | Patel et al. |
| 2003/0036797 A1 | 2/2003 | Malaviya et al. |
| 2005/0013870 A1 | 1/2005 | Freyman et al. |
| 2005/0124560 A1 | 6/2005 | Sung et al. |
| 2005/0181016 A1 | 8/2005 | Freyman et al. |
| 2006/0039896 A1 | 2/2006 | Kleinsek et al. |
| 2006/0136028 A1 | 6/2006 | Ross et al. |
| 2006/0147492 A1 | 7/2006 | Hunter et al. |
| 2006/0161265 A1 | 7/2006 | Levine et al. |
| 2006/0204738 A1 | 9/2006 | Dubrow et al. |
| 2006/0206139 A1 | 9/2006 | Tekulve |
| 2007/0014868 A1 | 1/2007 | Matheny |
| 2007/0014869 A1 | 1/2007 | Matheny |
| 2007/0014870 A1 | 1/2007 | Matheny |
| 2007/0014871 A1 | 1/2007 | Matheny |
| 2007/0014872 A1 | 1/2007 | Matheny et al. |
| 2007/0014873 A1 | 1/2007 | Matheny |
| 2007/0014874 A1 | 1/2007 | Matheny |
| 2007/0166396 A1 | 7/2007 | Badylak et al. |
| 2007/0168021 A1 | 7/2007 | Holmes, Jr. et al. |
| 2007/0208420 A1 | 9/2007 | Ameer et al. |
| 2008/0125851 A1 | 5/2008 | Kilpatrick et al. |
| 2008/0132922 A1 | 6/2008 | Buevich et al. |
| 2008/0175980 A1 | 7/2008 | Sun |
| 2008/0199507 A1 | 8/2008 | Skarja et al. |
| 2008/0274184 A1 | 11/2008 | Hunt |
| 2008/0281418 A1 | 11/2008 | Firestone |
| 2009/0130162 A2 | 5/2009 | Pathak et al. |
| 2009/0138074 A1 | 5/2009 | Freyman et al. |
| 2009/0163951 A1 | 6/2009 | Simmons et al. |
| 2009/0196910 A1 | 8/2009 | Yie et al. |
| 2009/0204228 A1 | 8/2009 | Hiles |
| 2009/0263453 A1 | 10/2009 | McKay et al. |
| 2009/0306688 A1 | 12/2009 | Patel et al. |
| 2010/0028396 A1 | 2/2010 | Ward et al. |
| 2010/0030292 A1 | 2/2010 | Sarkar et al. |
| 2010/0047305 A1 | 2/2010 | Naughton et al. |
| 2010/0168808 A1 | 7/2010 | Citron |
| 2010/0222882 A1 | 9/2010 | Badylak et al. |
| 2010/0233235 A1 | 9/2010 | Matheny et al. |
| 2010/0239632 A1 | 9/2010 | Walsh |
| 2010/0262221 A1 | 10/2010 | Schafer et al. |
| 2010/0266654 A1 | 10/2010 | Hodde et al. |
| 2011/0077455 A1 | 3/2011 | Duncan et al. |
| 2011/0166673 A1 | 7/2011 | Patel et al. |
| 2012/0034191 A1 | 2/2012 | Matheny |
| 2012/0100185 A1 | 4/2012 | Wen et al. |
| 2012/0156255 A1 | 6/2012 | Singh et al. |
| 2012/0183987 A1 | 7/2012 | Gevaert et al. |
| 2012/0302499 A1 | 11/2012 | Matheny |
| 2013/0023721 A1 | 1/2013 | Matheny |
| 2013/0122108 A1 | 5/2013 | Matheny |
| 2013/0126188 A1 | 5/2013 | Quitberg |
| 2013/0144356 A1 | 6/2013 | Horn et al. |
| 2014/0023723 A1 | 1/2014 | Leach et al. |
| 2014/0088339 A1 | 3/2014 | Matheny |
| 2014/0148897 A1 | 5/2014 | Matheny |
| 2014/0205565 A1 | 7/2014 | Matheny |
| 2014/0249623 A1 | 9/2014 | Matheny |
| 2014/0342984 A1 | 11/2014 | Matheny |
| 2014/0343673 A1 | 11/2014 | Matheny |
| 2015/0093353 A1 | 4/2015 | Matheny |
| 2015/0100115 A1 | 4/2015 | Matheny |
| 2015/0335787 A1 | 11/2015 | Matheny |
| 2015/0352145 A1 | 12/2015 | Matheny |
| 2015/0352257 A1 | 12/2015 | Early |
| 2015/0359942 A1 | 12/2015 | Matheny et al. |
| 2016/0008514 A1 | 1/2016 | Jones |
| 2016/0082153 A1 | 3/2016 | Matheny |
| 2016/0082154 A1 | 3/2016 | Matheny |
| 2017/0304507 A1 | 10/2017 | Matheny |
| 2017/0360544 A1 | 12/2017 | Ward et al. |
| 2018/0098836 A1 | 4/2018 | Lee et al. |
| 2018/0272136 A1 | 9/2018 | Horn et al. |
| 2019/0117836 A1 | 4/2019 | Matheny |
| 2019/0224368 A1 | 7/2019 | Matheny |
| 2019/0314551 A1 | 10/2019 | Matheny |
| 2020/0139011 A1 | 5/2020 | Vo et al. |
| 2020/0368393 A1 | 11/2020 | Matheny |
| 2020/0397945 A1 | 12/2020 | Matheny |
| 2021/0275723 A1 | 9/2021 | Matheny |
| 2022/0047777 A1 | 2/2022 | Zhang et al. |
| 2023/0026971 A1 | 1/2023 | Matheny |

FOREIGN PATENT DOCUMENTS

| | | |
|---|---|---|
| WO | 2002067895 A2 | 9/2002 |
| WO | 2004110427 A1 | 12/2004 |
| WO | 2005097219 A2 | 10/2005 |

(56) References Cited

FOREIGN PATENT DOCUMENTS

| WO | 2007011644 A2 | 1/2007 |
|---|---|---|
| WO | 2010014021 A1 | 2/2010 |
| WO | 2010096458 A1 | 8/2010 |
| WO | 2012018680 A1 | 2/2012 |
| WO | 2014046741 A1 | 3/2014 |
| WO | 2014046744 A1 | 3/2014 |
| WO | 2014046752 A1 | 3/2014 |
| WO | 2014046753 A2 | 3/2014 |
| WO | 2016022250 A1 | 2/2016 |
| WO | 2016093863 A1 | 6/2016 |
| WO | 2018017611 A1 | 1/2018 |

OTHER PUBLICATIONS

Badylak et al. "Xenogeneic Extracellular Matrix as a Scaffold for Tissue Reconstruction" 2004, Transplant Immunology 12:367-377.

Cottagnoud "Vancomycin Acts Synergistically with Gentamicin against Penicillin-Resistant Pneumococci by Increasing the Intracellular Penetration of Gentamicin" Jan. 2003, Antimicrob Agents Chemother. 47(1): 144-147.

European Search Report and Written Opinion for EP10808431.0, 08 Pages.

Gilbert et al. "Quantification of DNA in Biologic Scaffold Materials" 2009, J. Surgical Research 152:135-139.

Hoganson et al. "Preserved Extracellular Matrix Components and Retained Biological Activity in Decellularized Porcine Mesothelium" Sep. 2010, Biomaterials 31(27):6934-6940, XP027124625.

International Search Report and Written Opinion for PCT/US2011/064115 dated Apr. 24, 2012, 9 Pages.

International Search Report and Written Opinion for PCT/US2019/058681 dated Jan. 27, 2020, 10 Pages.

International Search Report and Written Opinion for PCT/US2021/046335 dated Nov. 29, 2021, 10 Pages.

Kumagai et al. "The Hmg-Coa Reductase Inhibitor Atorvastatin Prevents Atrial Fibrillation by Inhibiting Inflammation in a Canine Sterile Pericarditis Model" Apr. 1, 2004, Cardiovascular Research 62(1):105-111, doi: 10.1016/J.CARDIORES.2004.01.018, ISSN 0008-6363, XP008036414.

Lindsey et al. "Extracellular Matrix Remodeling Following Myocardial Injury" 2003, Annals of Medicine, 35:316-326.

Rai et al. "Synthesis, Properties and Biomedical Applications of Poly(Glycerol Sebacate) (Pgs): A Review" Feb. 4, 2012, Progress in Polymer Science, 37:1051-1078.

Robinson et al. "Extracellular Matrix Scaffold for Cardiac Repair" Aug. 30, 2005, Circulation 112(9), Supply I:135-143, XP055078062.

Shandling et al. "Dacron-Woven Pacemaker Pouch-Influence on Long-term Pacemaker Mobility Chest" Mar. 1991, Chest 99(3):660-662.

Temple University Health System; "Stem cell exosomes used to induce damaged mouse hearts to self-repair", ScienceDaily Jun. 18, 2015. www.sciencedaily.com/releases/2015/06/150618122104.htm.

TY RX Pharma AIGIS RX: "Antibacterial Envelope Informational Brochure" 2012, 4 Pages.

* cited by examiner

EXTRACELLULAR MATRIX (ECM) STRUCTURES FOR TISSUE REGENERATION

CROSS-REFERENCES TO RELATED APPLICATIONS

This application is a continuation of U.S. patent application Ser. No. 16/418,063, which is a continuation-in-part of U.S. patent application Ser. No. 14/685,714, filed Apr. 14, 2015, now U.S. Pat. No. 10,293,084; which is a continuation of U.S. patent application Ser. No. 14/306,368, filed Jun. 17, 2014, now U.S. Pat. No. 9,333,277; which is a continuation of U.S. patent application Ser. No. 13/033,102, filed Feb. 23, 2011, now U.S. Pat. No. 8,758,448; which is a continuation of U.S. patent application Ser. No. 12/394,914, filed Feb. 27, 2009, now abandoned; which is a continuation of U.S. patent application Ser. No. 11/747,004, filed May 10, 2007, now abandoned. The contents of these applications are incorporated herein by reference in their entireties.

FIELD OF THE INVENTION

The invention relates to articles and compositions having two or more forms of extracellular matrix.

BACKGROUND OF THE INVENTION

Tissue regeneration has been accomplished by using extracellular matrix material derived from mammalian tissues. Some of these mammalian tissues that have been described in patent literature include small intestine submucosa (SIS), liver basement membrane (LBM), urinary bladder submucosa (UBS) and stomach submucosa (SS). See U.S. Pat. Nos. 5,554,389, 4,902,508, and 5,281,422. Enamel matrices, which are the extracellular matrix around forming teeth, are described in U.S. Pat. No. 7,033,611. Extracellular matrices from these tissues have been isolated and dried to become solid materials (sheets and particulates). Particulate forms can be rehydrated in a suitable buffer to become fluidized or emulsive forms. Presently, these extracellular matrix compositions are used for tissue grafting, wound healing, and tissue regenerative purposes, (cite WSJ article).

It would be advantageous to the field of tissue engineering to invent articles and compositions for effecting improved tissue regeneration.

SUMMARY OF THE INVENTION

The invention is an article for wound healing and tissue regeneration comprising two or more sheets of mammalian extracellular matrix, said sheets of mammalian extracellular matrix laminated to each other to form a planar laminated article of mammalian extracellular matrix.

The invention is an article for wound healing and tissue regeneration comprising two or more sheets of mammalian extracellular matrix, said sheets of mammalian extracellular matrix laminated to each other to form a planar laminated article of mammalian extracellular matrix, said article further comprising in between at least two of said sheets at least one cell to further effect wound healing or tissue regeneration upon placement of said laminated article in a mammal at a site in said mammal in need of wound healing or tissue regeneration.

In the article the cell can be a stem cell. The cell can be a mesenchymal cell.

The invention is also a method comprising: identifying a defect or wound in mammalian tissue which could benefit from tissue regeneration or wound healing, providing an article comprising two or more sheets of mammalian extracellular matrix, said sheets of mammalian extracellular matrix laminated to each other to form a planar laminated article of mammalian extracellular matrix, contacting said defect or wound with said article, and regenerating tissue at said defect or healing said wound thereby.

DETAILED DESCRIPTION OF THE INVENTION

Figure 1A:
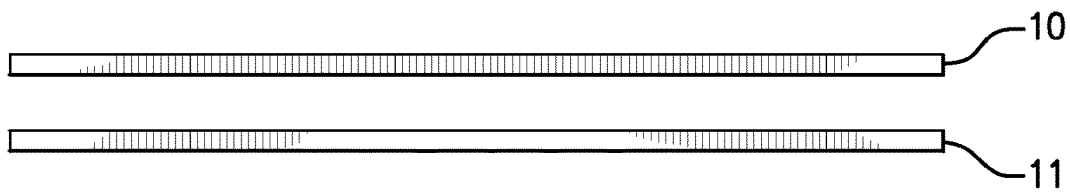
FIG. 1A, FIG. 1B, FIG. 1C, FIG. 1D, and FIG. 1E each depict laminate sheets of extracellular matrix forming a laminate extracellular matrix article.
Figure 1B:
Figure 1C:
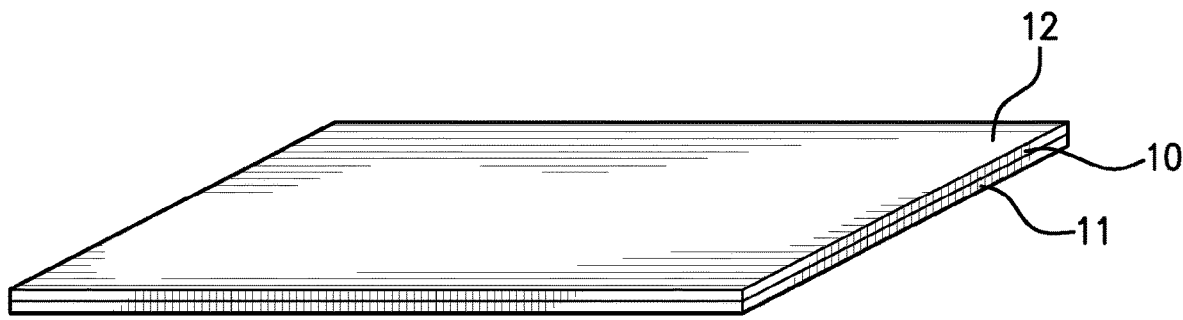
Figure 1D:
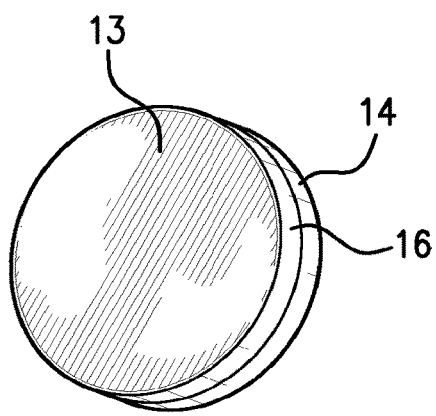
Figure 1E:
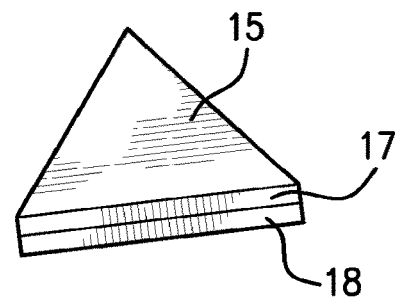

The invention is an article made of extracellular matrix for placing in a mammal at a site in need of tissue regeneration or wound healing to cause tissue regeneration and wound healing. These articles are made from extracellular matrices that are derived from one or more than one tissue source in one or more donor mammals.

The article is a laminate of two or more sheets of extracellular matrix. Accordingly, two components of such an article are first and second sheets of extracellular matrix, that are laminated together to form a laminate of extracellular matrix sheets. The two sheets in this example can be from the same source of extracellular matrix, i.e. both or all from SIS from a pig. The sheets can also be from different tissue sources of extracellular matrix, for example the first sheet is SIS, and the second sheet is SS. Both the SIS and SS can be from the same species of mammal (e.g. pig) or each from a different species of mammal (SIS from pig, and SS from cow). If there are 3 sheets in the laminate article all 3 can be SIS, or the first sheet can be SIS, the second SS, and the third sheet can be SIS, for example. These three sheets can be from the same species of mammal, i.e. a pig, or different mammalian species, i.e. the SIS sheets can be from a pig and the SS sheet can be from a cow.

Advantages are to be derived from using sheets of extracellular matrix from different mammalian tissues, where, for example, each tissue source provides certain attributes. For example, SIS provides tensile strength and the kind of support to newly forming tissue that one would attribute to small intestine submucosa. Adding a sheet from a different tissue, for example one without the tensile strength, but with other regenerative attributes, for example liver basement membrane (LBM), can lend to the article that is a laminate of sheets, an advantageous quality, particularly when two such sheets are laminate together. A sandwich configuration of such sheets can be formed, for example with two outer sheets having relatively substantial tensile strength and an inner sheet of something less strong having other attributes, such as LBM. A SIS-LBM-SIS sheet sandwich may provide the appropriate matrix for tissue regeneration for certain tissues in the body having certain requirements both for strength and regenerative potential.

The article can be two sheets of extracellular matrix encasing a composition. The composition can be any dispersible composition comprising a cell or cells that can rest upon a sheet of extracellular matrix and be covered (and encased by) another sheet. The composition can comprise a cell or cells, such as for example a plurality of stem cells that can aide and promulgate tissue regeneration from the article after placement in the patient. So then, for example the sheets can be SIS and the composition can comprise LBM, or the sheets can be SIS and the gel composition can also be SIS.

For any of these articles, the sheets can be laminated to each other at the edges around an amount of composition (comprising for example cells and other components) that then becomes encased in the two sheets upon lamination of the outer sheets to each other. The lamination of the two outer sheets together can be partial or complete, so that the composition can be entirely contained within the two sheets, or can be permitted to ooze out from between the sheets upon placement in the subject receiving treatment. The composition comprising the cells can also be a composition that supports the cells and allows them to survive and differentiate in that environment.

In another embodiment the sheets can encase one or more cells. The cell or cells can be stem cells. The sheet sandwich can act as support for the growth and development of the cells once placed in the body. The cell or cells can advantageously work in the article to regenerate tissue, or heal damaged tissue in conjunction with the extracellular matrix sheets. The cell or cells can be part of a composition comprising such cells, such as cell media or other material that will help promote the cell survival and differentiation.

The cell in the composition can be any cell, such as, for example a human embryonic stem cell, a fetal cardiomyocyte, a myofibroblast, a mesenchymal stem cell, an auto-transplanted expanded cardiomyocyte, an adipocyte, a totipotent cell, a pluripotent cell, a blood stem cell, a myoblast, a bone marrow cell, a mesenchymal cell, an embryonic stem cell, a parenchymal cell, an epithelial cell, an endothelial cell, a mesothelial cell, a fibroblast, a myofibroblast, an osteoblast, a chondrocyte, an exogenous cell, an endogenous cell, a stem cell, a hematopoetic stem cell, a pluripotent stem cell, a bone marrow-derived progenitor cell, a progenitor cell, a myocardial cell, a skeletal cell, a fetal cell, an embryonic cell, an undifferentiated cell, a multi-potent progenitor cell, a unipotent progenitor cell, a monocyte, a cardiomyocyte, a cardiac myoblast, a skeletal myoblast, a macrophage, a capillary endothelial cell, a xenogenic cell, an allogenic cell, an adult stem cell, and a post-natal stem cell. This list is not intended to be exhaustive.

The composition comprising a cell or cells can comprise any material supportive of the purposes of the article and cell culture, cell survival and differentiation. Thus, for example, the composition can comprise extracellular matrix that supports cells in culture and in vivo. The composition can comprise any material supportive of the purposes of the composition and the article in general, such as for example tissue regeneration, wound healing, cell culturing and survival, cell differentiation, stem cell recruitment and the like.

Any composition to support the cells such as an extracellular matrix composition can comprise such forms of extracellular matrix as an emulsion, gel, liquid, paste or particulate placed in between the sheets of matrix can be of mixed source of extracellular matrix, so that for example the gel can be a 50:50 mixture of LBM and UBS. The composition can also be a mixture of LBM and UBS. Thus, the composition can be some mixture or ratio of extracellular matrix from one or more tissue sources.

Generally, for any of the articles of the invention, the components such as sheets of extracellular matrix can be from the same mammalian tissue source (e.g. SIS) or they can be from different tissue sources (e.g. a SIS sheet and an LBM emulsion). Mammalian tissue sources are in general any tissue having an extracellular matrix that can be isolated from a mammal and decellularized. Thus for example, most mammalian organs are tissue sources. The tissue sources can be for example any mammalian tissue, including but not limited to the small intestine, large intestine, stomach, lung, liver, kidney, pancreas, placenta, heart, bladder, prostate, tissue surrounding growing tooth enamel, tissue surrounding growing bone, and any fetal tissue from any mammalian organ.

The forms of the extracellular matrices that make up the articles are generally sheets, although the sheets can be in any shape or size necessary for the site. Thus, for example the sheets can be square, rectangular, triangular, or circular. The sheets can be large or small, depending once again on the site that the article is to be placed.

Placement of the articles in the patients can be accomplished by any reasonable means, including simply placing the article at the site of defect, or attaching the article in place, e.g. by glue or suture.

Extracellular matrix can be obtained from the tissues of mammals by processes such as described in U.S. Pat. Nos. 5,554,389, 4,902,508, and 5,281,422. For example, the urinary bladder submucosa is an extracellular matrix that has the tunica mucosa (which includes the transitional epithelial layer and the tunica propria), a submucosal layer, 3 layers of muscularis, and the adventitia (a loose connective tissue layer). This general configuration is true also for small intestine submucosa (SIS) and stomach submucosa (SS). Obtaining enamel matrices is described in U.S. Pat. No. 7,033,611. Enamel matrix is extracellular matrix existing near forming teeth.

Other tissues such as the liver and pancreas have a basement membrane that does not demonstrate the kind of tensile strength of the tissues defined as submucosa. However, other useful properties may be opportunistically employed from the extracellular matrices of such tissues as the liver, pancreas, placenta and lung tissues which have either basement membrane for extracellular matrix or interstitial membrane (as with the lung). These softer matrices support cells such as those in the organs from which the matrices are derived. Thus, certain benefits are to be found in using the extracellular matrices of these tissues, especially in combination with other such matrices like SIS and SS that may be stronger and which offer their particular advantages. The extracellular matrices surrounding developing tooth enamel and developing bone also have particular advantages over other matrices in that they support the growth and differentiation of the hard tissues of bone and enamel.

Matrices can be used in whole or in part, so that for example, an extracellular matrix can contain just the basement membrane (or transitional epithelial layer) with the sub-adjacent tunica propria, the tunica submucosa, tunica muscularis, and tunica serosa. The matrix composition can contain any or all of these layers, and thus could conceivably contain only the basement membrane portion, excluding the submucosa. However, generally, and especially since the submucosa is thought to contain and support the active growth factors and other proteins necessary for in vivo tissue regeneration, the matrix composition from any given source will contain the active extracellular matrix portions that support cell development and differentiation and tissue regeneration. Thus it is generally understood by persons of skill in the art that the extracellular matrix of any of the mammalian tissue consists of several basically inseparable layers broadly termed extracellular matrix. Where layers can be separated these separate layers can electively be included in the composition, depending on whether they serve the purpose that is the goal of the article being made.

The sheets can come from one or more sources of mammalian extracellular matrix. Thus, for example, the composition can comprise extracellular matrix combinations from such sources as, for example but not limited to, small intestine submucosa, liver basement membrane, stomach submucosa, urinary bladder submucosa, placental basement membrane, pancreatic basement membrane, large intestine submucosa, lung interstitial membrane, respiratory tract submucosa, heart extracellular matrix, dermal matrix, and in general extracellular matrix from any mammalian fetal tissue. Generally a given sheet will be of one source of extracellular matrix, but if the article has two sheets, one sheet can be from one tissue source, and the second sheet can be from a second, different, tissue source.

The compositions of the invention can be made as follows: cells are selected for seeding and placing in between the sheets of extracellular matrix. The cell media is selected and the cells cultured to viability and then placed in the article.

In making the laminates, the ends of the sheets can be sealed using any reasonable means to do so, such as for example gluing or suturing the sheets to each other to form the article. If the sheets are encasing a composition comprising a cell or cells, the sheets are laminated at the outside edges and will encase the cells or cell composition. If a single sheet is folded over to encase a composition, lamination occurs on three sides of the sheet. If a rectangular, or other-shaped article is constructed from two or more sheets in a laminate, lamination occurs at the edges of the article to seal the composition inside, or to affix the sheets together.

For example, sheets can be laminated or layered with each other, so that a sheet of SIS can be placed with a sheet of SS, either with two sheets together SIS-SS or as a sandwich with three sheets, for example SIS-SS-SIS. Also, a different sandwich configuration can be made with two sheets of SIS or SS, sandwiching a gelatinous semi-solid or a solid powder (particulate) form of the matrix. The sandwich can be closed so that a composition can be placed securely between the two outer sheets. A single sheet can alternatively be folded over to encase an amount of composition.

Turning now to the figures, FIG. 1 depicts the laminate sheets in a rectangle shape, and circular and triangle shapes. FIG. 1A depicts a first rectangular sheet 10, and second rectangular sheet 11, before lamination. FIG. 1B depicts rectangular sheet 10 and rectangular sheet 11 laminated together to form laminated article 12. FIG. 1C depicts laminated article 12, having sheets 10 and 11 laminated together in a 3-dimensional perspective to form rectangular laminated article 12. FIG. 1D depicts circular laminated article 13 having laminated circular sheets 14 and 16 laminated together. FIG. 1E depicts laminated article 15 having a triangular shape, formed by lamination of triangular sheets 17 and 18 being laminated together.

Figure 2A:
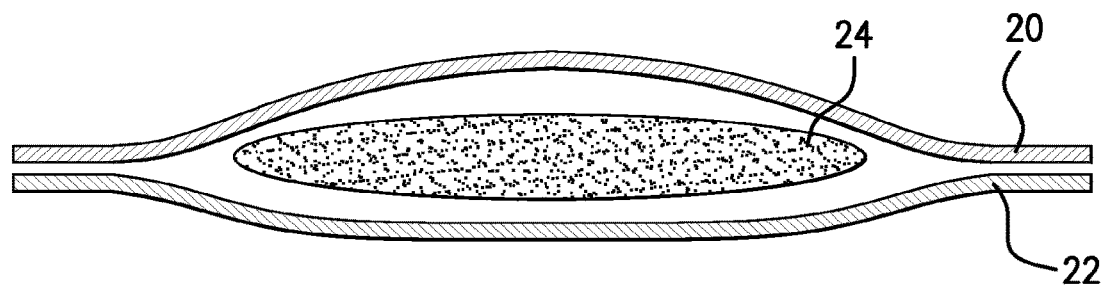
FIG. 2A, FIG. 2B, FIG. 2C, and FIG. 2D each depict an article having two sheets of extracellular matrix encasing a composition comprising a cell or a plurality of cells.
Figure 2B:
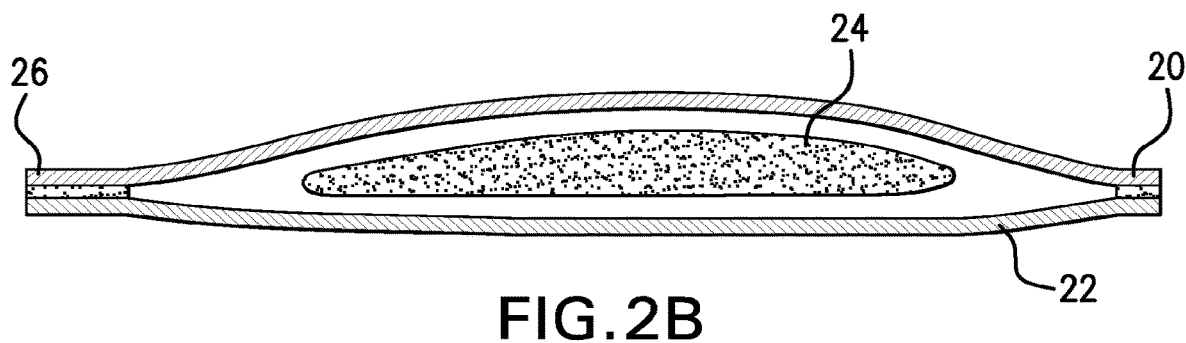
Figure 2C:
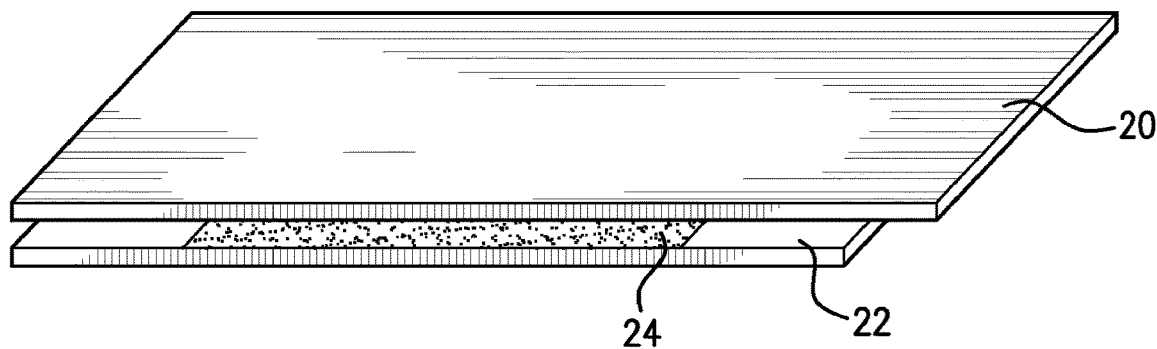
Figure 2D:
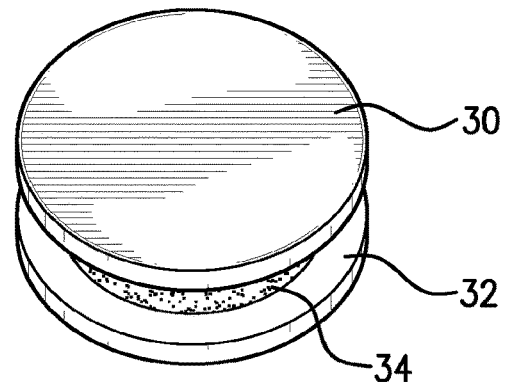

FIG. 2A depicts two sheets, a top sheet 20 and a bottom sheet 22, overlaying a composition 24 comprising cells. FIG. 2B depicts a cross sectional view of the top sheet 20 and bottom sheet 22 laminated at point 26 to encase composition 24. FIG. 2C depicts a 3-dimensional view of top sheet 20 and bottom sheet 22 with composition 24 in between the two sheets, ready for lamination. FIG. 2D depicts a circular article having top sheet 30 and bottom sheet 32 with composition 34 in between them, ready for lamination to close the edges and prepare the article for insertion into a mammalian patient.

Figure 3A:
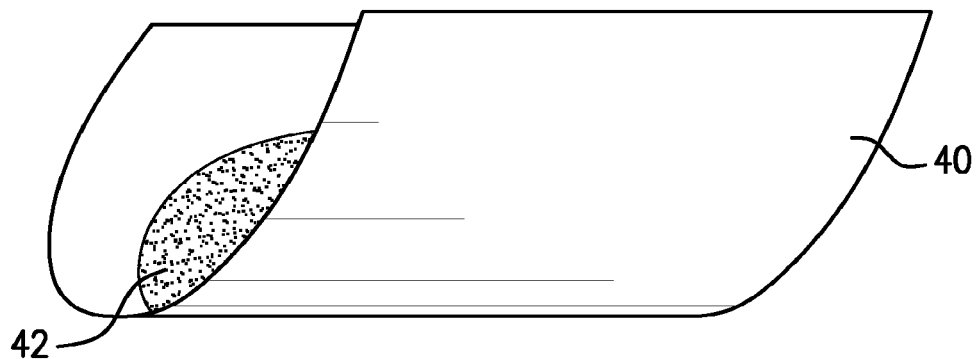
FIG. 3A, FIG. 3B, and FIG. 3C each depict an article having a single sheet of extracellular matrix that is folded over a composition comprising a cell or a plurality of cells.
Figure 3B:
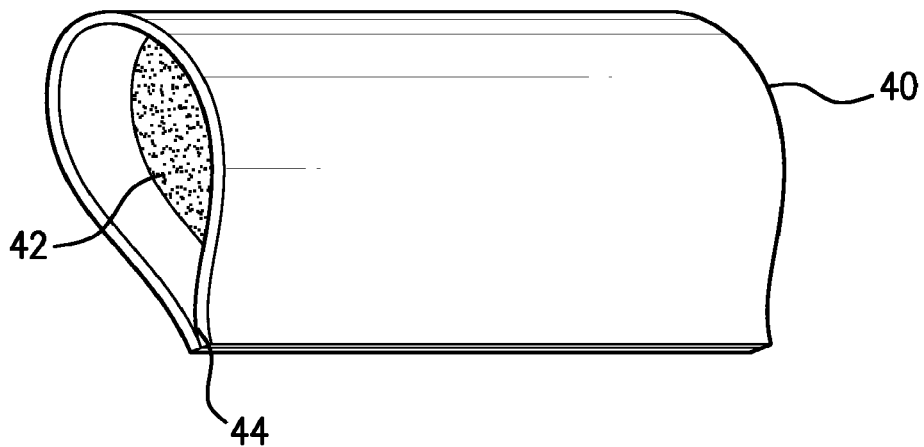
Figure 3C:
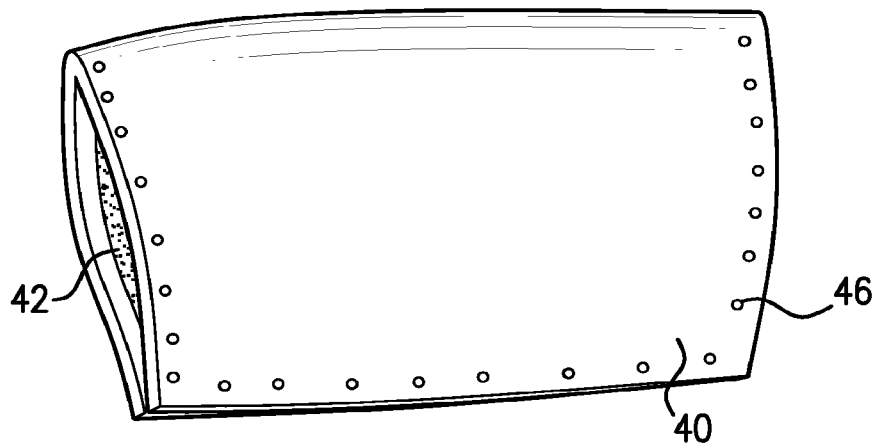

FIG. 3A depicts single sheet 40 encasing composition 42. FIG. 3B depicts single sheet 40 encasing composition 42 having laminated edge 44. FIG. 3C depicts single sheet 40 having composition 42 with laminate points 46 on 3 sides of the article.

The laminate article can encase a composition. The composition can comprise a cell or a plurality of cells. The composition can comprise a stem cell or a plurality of stem cells. The composition can be a material that supports the culturing of the cells. The composition can comprise extracellular matrix in gel or emulsion form that supports cell growth and survival.

The composition that might be encased in one or two sheets of extracellular matrix in addition to comprising a cell or cells might further comprise an additional component. The additional component can be any component that somehow serves the composition and its purpose in the mammalian body. Thus, the additional component can help to regenerate tissue, heal a wound, better cultivate cells in the composition, better recruit endogenous stem cells once in the body, manipulate the immune environment in a beneficial way, therapeutically treat the local environment, or otherwise contribute to some aspect of the process for which the composition and article that includes the composition is being used.

Thus, the additional component can be a protein or a drug.

The protein can be for example a growth factor, or any other type or protein that might stimulate some part of the tissue regenerative process, a collagen, a proteoglycan, a glycosaminoglycan (GAG) chain, a glycoprotein, a growth factor, a cytokine, a cell-surface associated protein, a cell adhesion molecule (CAM), an angiogenic growth factor, an endothelial ligand, a matrikine, a matrix metalloprotease, a cadherin, an immunoglobin, a fibril collagen, a non-fibrillar collagen, a basement membrane collagen, a multiplexin, a small leucine rich proteoglycan, decorin, biglycan, a fibromodulin, keratocan, lumican, epiphycan, a heparan sulfate proteoglycan, perlecan, agrin, testican, syndecan, glypican, serglycin, selectin, a lectican, aggrecan, versican, nuerocan, brevican, cytoplasmic domain-44 (CD-44), macrophage stimulating factor, amyloid precursor protein, heparin, chondroitin sulfate B (dermatan sulfate), chondroitin sulfate A, heparan sulfate, hyaluronic acid, fibronectin (Fn), tenascin, elastin, fibrillin, laminin, nidogen/entactin, fibulin I, fibulin II, integrin, a transmembrane molecule, platelet derived growth factor (PDGF), epidermal growth factor (EGF), transforming growth factor alpha (TGF-alpha), transforming growth factor beta (TGF-beta), fibroblast growth factor-2 (FGF-2) (also called basic fibroblast growth factor (bFGF)), thrombospondin, osteopontin, angiotensin converting enzyme (ACE), and vascular epithelial growth factor (VEGF). This list is not intended to be exhaustive.

The additional component can also be a drug, such as an agent that has therapeutic properties. The drug can be bioactive and play some role in the process of tissue regeneration or act as an antibiotic, antiviral, or other active therapeutic agent serving a purpose in the composition as a whole. The drug can be a small molecule, or any other agent having therapeutic properties.

The invention contemplates using the articles of the invention for contacting a defect in mammalian tissue. The defect can be a cut, disease, wound, burn, scar, necrosis, or other abnormality that would be beneficial to treat. Regenerating tissue at the defect can be one response elicited from the step of placing the extracellular matrix composition in contact with the defect. If the defect is a wound in need of healing, wound healing may be another response that occurs as a result of placing the extracellular matrix at the wound site. In general any term that identifies that the tissue could benefit from a healing or tissue regeneration fits within the scope of the use for the composition. Thus regenerating tissue, or healing a wound are two but the not the only phrases that can be used to describe the effects achieved when the composition is placed in the mammal at a site of defect or damage in tissue.

Therapeutically effective amount is a term meant to capture the idea that you need to apply enough of the composition in sufficient strength so that the composition can have a positive effect on the tissue that is being treated in the subject. The amount may therefore apply to an amount of cell or cells in the composition encased by the laminate. That the amount is therapeutically effective is determined by the composition's ability to have an effect on the regenerative or wound healing activity provided by the article (that encases the composition) as a whole at the site where the article (and composition) contacts the tissue. A therapeutically effective amount is determinable by routine testing in patients with wounds or defects. In general a minimal therapeutically effective amount would be considered sufficient cells (or sufficient amount of an additional component) in the composition to effect the wound healing or tissue regeneration at the site of placement of the article that contains the cells or the additional component.

Regenerating tissue, as is accomplished by placing an article of the invention in a mammal in need of tissue regeneration, is the ability to make tissue regrow, an organ regrow itself, and for tissue to reform or new tissue to form without scarring. Healing a wound is the ability of the tissue to heal preferably without scarring or with very minimal scarring.

All references cited are incorporated in their entirety. Although the foregoing invention has been described in detail for purposes of clarity of understanding, it will be obvious that certain modifications may be practiced within the scope of the appended claims.

The invention claimed is:

1. An article comprising:
a bioremodelable pouch structure comprising an extracellular matrix (ECM) structure in sheet form, said ECM structure comprising ECM from a decellularized mammalian tissue source, said decellularized mammalian tissue source being small intestine submucosa, liver basement membrane, stomach submucosa, urinary bladder submucosa, placental basement membrane, pancreatic basement membrane, large intestine submucosa, lung interstitial membrane, respiratory tract submucosa, heart extracellular matrix, or dermal matrix;
said pouch structure comprising an internal cavity having an opening;
wherein the ECM structure provides tensile strength to support newly forming tissue and includes first and second ECM sheets or sheet portions, each ECM sheet or sheet portion having single or plural layers and edges, wherein only the edges of the ECM sheets or sheet portions are joined together by laminating, suturing or gluing except for the edges that form the opening to provide the internal cavity that is located between the sheets or sheet portions; and
wherein the pouch structure is configured to contain an additional component or a composition.

2. The article of claim 1, wherein the pouch structure supports tissue regeneration, wound healing, or new tissue formation when placed in a mammal.

3. The article of claim 1, wherein the edges are joined together by suturing.

4. The article of claim 1, wherein the pouch structure has a rectangular configuration with a closed end, and only the edges of both sides of the ECM sheet portions adjacent the closed end are joined together.

5. The article of claim 1, wherein the composition is a drug.

6. The article of claim 1, wherein the composition comprises an active therapeutic agent.

7. The article of claim 1, wherein the composition comprises an antibiotic.

8. The article of claim 1, wherein the composition is contained within the internal cavity of the pouch structure, and wherein the edges are partially joined.

9. The article of claim 1, wherein the pouch has a periphery that is round.

10. The article of claim 1, wherein the pouch has a periphery that is generally rectangular.

11. The article of claim 1, wherein each ECM sheet includes 2 or 3 layers of SIS material.

12. The article of claim 11, wherein the layers of SIS material are laminated together.

13. The article of claim 12, wherein the pouch structure is configured to contain the additional component or the composition between the layers of SIS material.

14. The article of claim 1, wherein the edges are laminated together.

15. The article of claim 14, wherein the pouch structure is configured to contain the additional component or the composition between the edges.

16. The article of claim 1, wherein each ECM sheet or sheet portion has plural layers, and wherein the pouch structure is configured to contain the additional component or the composition between at least two of the plural layers.

* * * * *